United States Patent
Magalhaes Mendes et al.

(10) Patent No.: US 10,273,589 B2
(45) Date of Patent: Apr. 30, 2019

(54) ELECTRODES/ELECTROLYTE ASSEMBLY, REACTOR AND METHOD FOR DIRECT AMINATION OF HYDROCARBONS

(71) Applicant: CUF-QUIMICOS INDUSTRIAIS S.A., Estarreja (PT)

(72) Inventors: Adelio Miguel Magalhaes Mendes, Oporto (PT); Alejandro Franca Gomes Ribeiro, Estarreja (PT); Margarida Dias Catarino, Sao Mamede de Infesta-matosinhos (PT); Ana Sofia Pimentel Felix, Vila Nova de Gaia (PT); Mario Jorge De Oliveira Pinho, Aveiro (PT)

(73) Assignee: CUF—QUIMICOS INDUSTRIAIS S.A., Estarreja (PT)

( * ) Notice: Subject to any disclaimer, the term of this patent is extended or adjusted under 35 U.S.C. 154(b) by 309 days.

(21) Appl. No.: 14/780,070

(22) PCT Filed: Mar. 28, 2014

(86) PCT No.: PCT/IB2014/060276
§ 371 (c)(1),
(2) Date: Sep. 25, 2015

(87) PCT Pub. No.: WO2014/155360
PCT Pub. Date: Oct. 2, 2014

(65) Prior Publication Data
US 2016/0032469 A1  Feb. 4, 2016

(30) Foreign Application Priority Data

Mar. 28, 2013 (PT) .......................................... 106860

(51) Int. Cl.
*C25B 11/04* (2006.01)
*C25B 3/00* (2006.01)
(Continued)

(52) U.S. Cl.
CPC ...... *C25B 11/0478* (2013.01); *B29C 37/0025* (2013.01); *B29C 43/203* (2013.01);
(Continued)

(58) Field of Classification Search
CPC ........... C25B 3/00; C25B 9/04; C25B 11/035; C25B 11/0478; C25B 11/0431;
(Continued)

(56) References Cited

U.S. PATENT DOCUMENTS

| | | |
|---|---|---|
| 3,919,155 A | 11/1975 | Squire |
| 3,929,889 A | 12/1975 | Squire |

(Continued)

FOREIGN PATENT DOCUMENTS

| | | |
|---|---|---|
| WO | 2007025882 A1 | 3/2007 |
| WO | 2011055343 A2 | 5/2011 |

OTHER PUBLICATIONS

R.S. Amado, et al; Pilhas a combustivel de oxido solido: materiais, componentos a configuracoes; Quim. Nova; vol. 30; No. 1; 2007; pp. 189-197 (English translation not available).
(Continued)

*Primary Examiner* — Ciel P Thomas
(74) *Attorney, Agent, or Firm* — Lucas & Mercanti, LLP

(57) ABSTRACT

An electrodes/electrolyte assembly—MEA, electrochemical membrane reactor—is described and a method for the direct amination of hydrocarbons, namely for the direct amination of benzene to aniline, and a method for the preparation of said electrodes/electrolyte assembly. The presented Solution allows the increase of conversion of said amination to above 60%, even at low temperatures, i.e., between 200° C. and 450° C.; preferably between 300° C. and 400° C. The electrodes/electrolyte assembly for direct amination of hydrocarbons comprises: an anode (1), electrons and protons conductor, that includes a composite porous matrix, com-
(Continued)

prised by a ceramic fraction and a catalyst for said amination at temperatures lower than 450° C.; a porous cathode (3), electrons and protons conductor, and electrocatalyst; an electrolyte (2), protons or ions conductor and electrically insulating, located between the anode (1) and the cathode (3), made of a composite ceramic impermeable to reagents and products of said amination.

18 Claims, 3 Drawing Sheets

(51) Int. Cl.
    *C25B 9/04*     (2006.01)
    *C25B 11/03*     (2006.01)
    *B29C 37/00*     (2006.01)
    *B29C 43/20*     (2006.01)
    *B29C 43/52*     (2006.01)
    B29K 29/00     (2006.01)
    B29K 105/16     (2006.01)
    B29K 505/00     (2006.01)
    B29L 31/34     (2006.01)

(52) U.S. Cl.
    CPC .............. *B29C 43/52* (2013.01); *C25B 3/00* (2013.01); *C25B 9/04* (2013.01); *C25B 11/035* (2013.01); *C25B 11/0431* (2013.01); *B29K 2029/04* (2013.01); *B29K 2105/16* (2013.01); *B29K 2505/00* (2013.01); *B29L 2031/34* (2013.01)

(58) Field of Classification Search
    CPC ... B29C 37/0025; B29C 43/203; B29C 43/52; B29K 2029/04; B29K 2105/16; B29K 2505/00; B29L 2031/34
    See application file for complete search history.

(56) References Cited

U.S. PATENT DOCUMENTS

| | | |
|---|---|---|
| 4,001,260 A | 1/1977 | Del Pesco |
| 4,031,106 A | 6/1977 | Del Pesco |
| 2003/0021900 A1 | 1/2003 | Jacobson et al. |
| 2005/0064259 A1* | 3/2005 | Coors .................... C25B 15/04 429/411 |
| 2007/0278092 A1* | 12/2007 | Irvine ...................... C25B 1/04 204/194 |
| 2009/0075138 A1 | 3/2009 | Sin Xicola et al. |
| 2011/0132770 A1* | 6/2011 | Sala ......................... C25B 3/04 205/338 |
| 2011/0189559 A1 | 8/2011 | De Miranda et al. |
| 2012/0231366 A1 | 9/2012 | Wachsman et al. |
| 2012/0273366 A1 | 11/2012 | Magalhaes Mendes |

OTHER PUBLICATIONS

D.Z. de Florio, et al; Materiais ceramicos para celulas a combustivel; Ceramica; vol. 50; 2004; pp. 275-290 (English translation not available).

Jeffery J. Haslam, et al; Effects of the use of pore formers on performance of an anode supported solid oxide fuel cell; J. Am. Ceram. Soc.; vol. 88; No. 3; 2005; pp. 513-518.

International Search Report dated Jul. 31, 2014 for Application No. PCT/IB2014/060276 and English translation.

* cited by examiner

ELECTRODES/ELECTROLYTE ASSEMBLY, REACTOR AND METHOD FOR DIRECT AMINATION OF HYDROCARBONS

CROSS REFERENCE TO RELATED APPLICATION

This Application is a 317 of PCT/IB2014/060276 filed on Mar. 28, 2014 which, in turn, claimed the priority of Portuguese Patent Application No. 106860 filed on Mar. 28, 2013, both applications are incorporated herein by reference.

FIELD OF INVENTION

The present invention describes an electrochemical cell or an electrodes/electrolyte assembly (usually referred in English as Membrane Electrode Assembly—MEA), a chemical/electrochemical reactor, and a method for the direct amination of hydrocarbons, namely the direct amination of benzene to aniline.

The MEA may be inserted into a membrane chemical/electrochemical reactor, preferably used for the direct amination of hydrocarbons, namely benzene. However, direct amination is a reaction strongly limited by thermodynamic equilibrium.

It has been verified that the MEA used in the chemical/electrochemical reactor allows an improved electrochemical pumping of the hydrogen formed inside the reaction medium, and electrochemical promotion of the amination reaction.

BACKGROUND OF THE INVENTION

The direct amination of benzene was first proposed in 1917 and since then efforts have been made to increase the conversion of this reaction limited by thermodynamic equilibrium. Best results reported until 2007 are presented in documents U.S. Pat. Nos. 3,919,155, 3,929,889, 4,001,260, and 4,031,106 from Dupont, which reveal a catalyst of Ni/NiO/ZrO$_2$ whose oxygen from nickel oxide reacts with the hydrogen formed in the amination, yielding water. This catalyst is regenerable after a chemical reaction. The reaction system allowed obtaining a conversion of about 13%, operating at 300° C., and at 300 bar.

Document WO 2007/025882 from BASF, describes the use of a palladium or palladium alloy membrane catalytic reactor to conduct the direct amination of benzene. A process is described, in which hydrogen is removed from the reaction system under the influence of the partial pressure difference between retentate (reaction medium) and permeate. To the permeate is applied a current of cleaning gas or even oxygen, with which the permeated hydrogen reacts, thus maintaining its partial pressure very low on the permeate side. According to the inventors, this system allows increasing the conversion of benzene to aniline in 20%.

Document WO 2011055343 describes an electrochemical reactor for direct amination of benzene, with electrochemical pumping of oxygen or hydrogen. This type of reactor is equipped with a ceramic electrolyte conductor of ions (of hydrogen or oxygen) and impermeable to non-ionic species. The purposed reactor works similarly to a fuel cell, where the oxidizing and reducing reactions occur in the electrodes located on both sides of the electrolyte. The configuration of this type of reactor is used to selectively supply oxygen to or remove hydrogen from the catalytic zone of the direct amination of benzene.

Fuel cells that use ceramic electrolytes are denominated solid oxide fuel cells (SOFC). These cells have gained special interest since they present advantages over other types of fuel cells (e.g., cells with polymeric electrolyte).

A solid electrolyte can operate at higher temperatures, thus favouring the kinetics of the chemical and electrochemical reactions, they can operate with direct feeding of hydrocarbons (with or without internal reforming), they are more stable mechanically, and they are chemically compatible with carbon monoxide. The first solid electrolytes proposed for fuel cells were composed of zirconium oxide stabilized with yttrium oxide (yttria stabilized zirconia—YSZ). These electrolytes, based on ceramic conducting oxygen ions are, still today, the most frequently used in solid oxide fuel cells, as they present a good ionic conductivity, are mechanically resistant, and are compatible with oxidising and reducing atmospheres. However, they have the drawback of their optimal operation temperature laying close to 800° C. [1, 2].

The development of new electrolytes based on the conduction of hydrogen ions has gained great support in recent years. Electrolytes based in cerium oxide have been replacing YSZ, as they allow lowering the operation temperature of the SOFC to about 500° C. Most common known electrolytes are those consisting of barium cerates doped with yttrium (yttria doped barium cerate—BCY). Those materials present considerable protonic conductivity values and a temperature lower than 600° C. Due to its characteristics this type of materials are most interesting for processes where separation and formation of hydrogen are necessary [1, 2].

SUMMARY

Present invention describes an electrodes/electrolyte assembly (Membrane Electrode Assembly—MEA), an electrochemical membrane reactor and a method for the direct amination of hydrocarbons, namely for the direct amination of benzene to aniline, and a method for the preparation of said electrodes/electrolyte assembly, (MEA). The presented solution allows the increase of conversion of direct amination of hydrocarbons to above 60%, even at low temperatures, i.e., at temperatures lower than 450° C., in particular between 200° C. and 450° C.; preferably between 300° C. and 400° C.

In one embodiment of the present invention the electrodes/electrolyte assembly (MEA) comprises:
- an anode, electrons and protons conductor, comprising a composite porous matrix comprised of a ceramic and a metal fraction—that is a cermet—where the metal is a catalyst of said amination at temperatures lower than 450° C., preferably between 200° C. and 450° C., more preferably between 300° C. and 400° C.;
- an electro catalysing porous cathode, having protonic and electronic conductivity;
- an electrolyte, protons or ions conductor and electrically insulating, located between the anode and the cathode, made of a composite ceramic impermeable to reagents and to the products of said amination.

In other embodiments of the described electrodes/electrolyte assembly (MEA) the anode porosity can range from 10% to 40%, preferably 30%.

In an embodiment, the electrodes/electrolyte assembly (MEA) allows even better results when it comprises:
- an anode, electrons and protons conductor, comprising a composite porous matrix comprised of a ceramic and a metal fraction—that is a cermet—where the metal is a catalyst of said amination at temperatures lower than 450° C., in particular between 200° C. and 450° C., preferably between 300° C. and 400° C.;

the anode porosity may range from 10% to 40%, preferably 20% to 30%, even more preferably 30%;

an electro catalysing porous cathode, having protonic and electronic conductivity;

an electrolyte, protons or ions conductor and electrically insulating, located between the anode and the cathode, made of a composite ceramic impermeable to reagents and products of said amination.

For best results of the electrodes/electrolyte assembly (MEA), the anode catalyst can comprise a doped metal with at least one element from the following list: aluminium, cobalt, copper, chromium, tin, strontium, iron, gadolinium, indium, iridium, yttrium, lanthanum, lithium, manganese, molybdenum, niobium, gold, palladium, platinum, silver, praseodymium, ruthenium, titanium, zinc, or mixtures thereof.

For best results from the electrode/electrolyte assembly (MEA), the anode metal may be nickel, nickel oxide or mixtures thereof.

For best results from the electrodes/electrolyte assembly (MEA), the matrix of the anode may comprise:

a ceramic that comprises at least one element from the following list: aluminum oxide, barium, calcium, cerium, copper, strontium, gadolinium, yttrium, lanthanum, niobium, neodymium, praseodymium, samarium, titanium, zirconium or mixtures thereof; including but not limited to: BCY, BaCaNbO (BCN), BaCaNbYO (BCNY), BaCeEuO (BCE), BaCeGdO (BCG), BaCeGdPrO (BCGP), BaCeIO (BCI), BaCeInO (BCIn), BaCeNdO (BCN), BaCeNbSmO (BCNS), BaCeSmO (BCS), BaCeSmCaO (BCSC), BaCeTaYO (BCTY), BaCeInYbO (BCIYb), BaNaNbFeO (BNF), BaTiErO (BTE), BaTiYO (BTY), BaZrYO (BZY), BaZrIO (BZI), BaZrCeYO (BZCY), BaZrPrYO (BZPY), CaZrInO (CZI), SrCaZrTaO (SCZT), SrCeYO (SCY), SrCeYbO (SCYb), SrZrYO (SZY);

at least one metal selected from the following list: aluminium, cobalt, copper, chromium, tin, strontium, iron, gadolinium, indium, iridium, yttrium, lanthanum, lithium, manganese, molybdenum, niobium, gold, palladium, platinum, silver, ruthenium, titanium, zinc, or mixtures thereof; namely but not exclusively: Cu—Co, Ni—Al, Ni—Co, Ni—Cu, Ni—Fe, Ni—La, Ni—Li—Ti, Ni—Mn, Ni—Mg, Cu—Zn—Ni, NbTiO, Ni—Pd, Ni—Pt, Pd—Ag, Pd—Pt, Ru—Ni, Sn—Ni, LaCaCrO (LCC), LaSrCrO (LSC), LaSrCrMnO (LSCM), LaSrTiO (LST), SrYTiO (SYT), SrMgMoO (SMM), ZrTiYO (ZTY).

For best results from the electrodes/electrolyte assembly (MEA), the ceramic support of the anode matrix can comprise barium cerate doped with yttrium—BaCeYO or BCY.

For best results from the electrodes/electrolyte assembly (MEA) the anode can comprise nanoparticulate Ni and BCY, where Ni is both electrons conducting and chemical catalyst (catalyst for the amination reaction) and electrochemical catalyst (catalyst for oxidizing the atomic or molecular hydrogen to protons), while further allowing protons conduction.

For best results from the electrodes/electrolyte assembly (MEA), the ceramic support of the anode matrix can comprise barium cerate doped with yttrium and zirconium.

For best results of the electrodes/electrolyte assembly (MEA) in terms of stability, the anode can comprise nickel and barium cerate doped with yttrium and zirconium (BaZrCeYO (BZCY)).

For best results from the electrodes/electrolyte assembly (MEA), the anode can comprise an homogeneous mixture of 30% (w/w) to 70% (w/w) of said catalyst/electronic conductor, preferably nickel oxide; and 70% (w/w) to 30%(w/w) of the ceramic fraction of the cermet, preferably BCY.

For best results from the electrodes/electrolyte assembly (MEA) of present invention, the electrolyte can comprise at least one element from the following list: aluminium, barium, calcium, cerium, copper, strontium, gadolinium, yttrium, indium, lanthanum, niobium, neodymium, praseodymium, samarium, titanium, zirconium, or mixtures thereof; preferably barium cerate doped with yttrium (BCY) or barium cerate doped with yttrium and zirconium (BZCY).

For best results from the electrodes/electrolyte assembly (MEA) of the present invention, the cathode can comprise at least one metal selected from the following list: aluminium, cobalt, copper, chromium, tin, strontium, iron, indium, iridium, yttrium, lithium, manganese, molybdenum, niobium, gold, palladium, platinum, silver, ruthenium, titanium, zinc. Namely nanoparticulate platinum or nanoparticulate platinum and BCY on the electrolyte.

For best results of the electrodes/electrolyte assembly (MEA) of the present invention, the cathode can comprise at least one element selected from the following list: aluminium, barium, calcium, cerium, copper, strontium, gadolinium, yttrium, lanthanum, niobium, neodymium, praseodymium, samarium, titanium, and zirconium.

For best results from the electrodes/electrolyte assembly (MEA) of the present invention, the cathode can be platinum, the anode can be nickel and barium cerate doped with yttrium, this particular configuration enhancing the efficiency of the conversion of benzene to aniline even at low temperatures.

Another aspect of present invention refers to an electrochemical reactor with electrochemical pumping of hydrogen for the direct amination of hydrocarbons, namely benzene to aniline; this reactor comprises at least one electrochemical cell which comprises at least one electrodes/electrolyte assembly (MEA) as described in this disclosure, an anode chamber, where referred amination occurs, and a cathode chamber, where the reduction of protons occurs. The anode and the cathode of said electrodes/electrolyte assembly are electrically connected, directly or through a power supply. The power supply imposes a difference of electric potential between the anode and cathode of said electrodes/electrolyte assembly, where the applied difference of potential can preferably range from 0.2 V to 1.5 V, preferably from 0.5 V to 1 V. The optimal difference of potential depends on the operating conditions of the reactor and of the MEA, and may be increased to avoid the deep dehydrogenation of reagents, i.e., the removal of more than one hydrogen atom per reagent molecule, preferably lower than 1.5 V. In this embodiment, molecular hydrogen produced in the cathode can be more easily removed by feeding an inert gas into this chamber, namely nitrogen or water vapour.

In other embodiments of the reactor, the anode is electrically and directly connected to the cathode, having the cathode chamber to be fed with an oxygen carrying gas, preferably air or pure oxygen. This embodiment is only possible if, for the observed differences in potential, a deep dehydrogenation of reagents doesn't occur.

In other embodiments, the operating temperature of the reactor described in present invention can range between 200° C. and 450° C.; preferably between 300° C. and 400° C.; surprisingly affording to maintain the conversion reaction of aniline above 60%. In other embodiments, the operating pressure of the described reactor can range between the atmospheric pressure and 300 bar, more preferably between 7 bar and 30 bar.

Other embodiments refer to a method for obtaining the electrodes/electrolyte assembly above described which comprises the following steps:

- obtaining an anode (1) by mixing a metallic and electrons conducting catalyst with a ceramic conducting protons and an organic additive; the proportion of metal oxide on the ions conductor ranges from 30% (w/w) to 70% (w/w), and the concentration of organic additive—preferably starch or polyvinyl alcohol—in the mixture, ranges between 5% (w/w) to 30% (w/w) in the presence or absence of a solvent;
- conforming the resulting mixture—the anode (1)—into a mould and pressing;
- depositing a layer of a ceramic composite impermeable to reagents and to the products of said amination—which corresponds to the electrolyte (2)—on the anode (1), and sintering at a temperature between 1300° C. and 1600° C. for 5 h to 24 h, with a heating rate of between 1° C.·min$^{-1}$ and 5° C.·min$^{-1}$ in an oxidising atmosphere;
- depositing the cathode (3) over the anode (1)/electrolyte (2) by co-pressing and co-sintering, spraying of the wet powder or direct application of commercial pastes;
- sintering the cathode at a temperature ranging from 900° C. to 1100° C., preferably during 1 h to 5 h, with a rate of heating that varies from 1° C.·min$^{-1}$ to 5° C.·min$^{-1}$, in an oxidising atmosphere.

In other embodiments of the method for obtaining the above described electrode/electrolyte assembly, the cathode (3) is comprised by one or more layers that are obtained after deposition of a thin layer of material upon the electrolyte and subsequent sintering, being the procedure repeated until the desired thickness and electronic conductivity is obtained.

In other embodiments of the described electrodes/electrolyte assembly (MEA) it can present a planar or tubular configuration, and can be obtained by deposition of the electrolyte and cathode upon the anode, followed by pressing and sintering. The thickness of the electrolyte can vary, preferably, between 10 µm and 400 µm, while the thickness of the anode can vary, preferably, between 100 µm and 1500 µm, and the thickness of the cathode can vary, preferably, between 1 µm and 100 µm. This preferred configuration increases the yield of conversion of benzene to aniline.

The present invention describes the method for preparation and application of an electrodes/electrolyte assembly (usually referred in English as Membrane Electrode Assembly—MEA) in the direct amination of hydrocarbons, namely the direct amination of benzene to aniline. The anode (1) is prepared using oxides conducting protons and metals, which are simultaneously active for the catalytic and direct amination of hydrocarbons, namely of benzene, and for an electro oxidizing reaction of atomic or molecular hydrogen that takes place in the electrodes. The unveiled anode (1) demonstrated to have a great activity for the amination of benzene, due to the ability of electrochemical pumping of atomic hydrogen and the consequent effect of electrochemical promotion of the amination reaction. The developed MEAs, when inserted in an electrochemical reactor, allow for the increase of conversion from the direct amination of benzene to aniline, ranging from 0.5% to about 90%, namely 50% to 60%.

The preferably and more preferably embodiments described are combinable.

Definitions:

Nanoparticles—Particles with a size inferior to 100 nm.

Nanodispersed—Dispersion that is verified even at the nanoscale, i.e. in a scale inferior to 100 nm.

Cathode chamber—Chamber adjacent to the cathode, where the reduction of hydrogen protons to molecular hydrogen, or its reaction with oxygen to form water, occurs.

Anode chamber—Chamber adjacent to the anode, where the amination and formation of atomic or molecular hydrogen reaction occurs.

Doped—Is said of a material to which another material has been added in a very low concentration, typically inferior to 1% (w/w).

BRIEF DESCRIPTION OF THE FIGURES

For easier comprehension of the invention the attached figures are annexed, which represent preferred embodiments of the invention that however are not intended to limit the present invention.

In a preferred embodiment of the invention, the direct amination of benzene to aniline is observed, where the benzene molecules and ammonia reagents are illustrated interacting with the anode where, upon the catalyst, takes place the activation of the reagents, the removal of one hydrogen atom from each reactant molecule, the oxidation of the hydrogen atoms at the surface of the catalyst, and the reaction of ammonium and benzene radicals to produce aniline. In this illustration it can be verified that there is no forming of molecular hydrogen.

Figure 1:
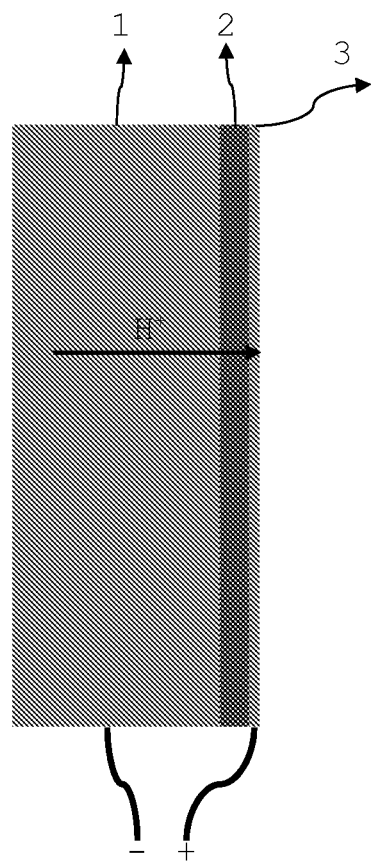
FIG. 1—Is a schematic representation of the cell or electrodes/electrolyte assembly (MEA):
- (1)—Represents the electrode in contact with the reaction medium—anode;
- (2)—Represents the electrolyte;
- (3)—Represents the electrode—cathode.
Figure 2:
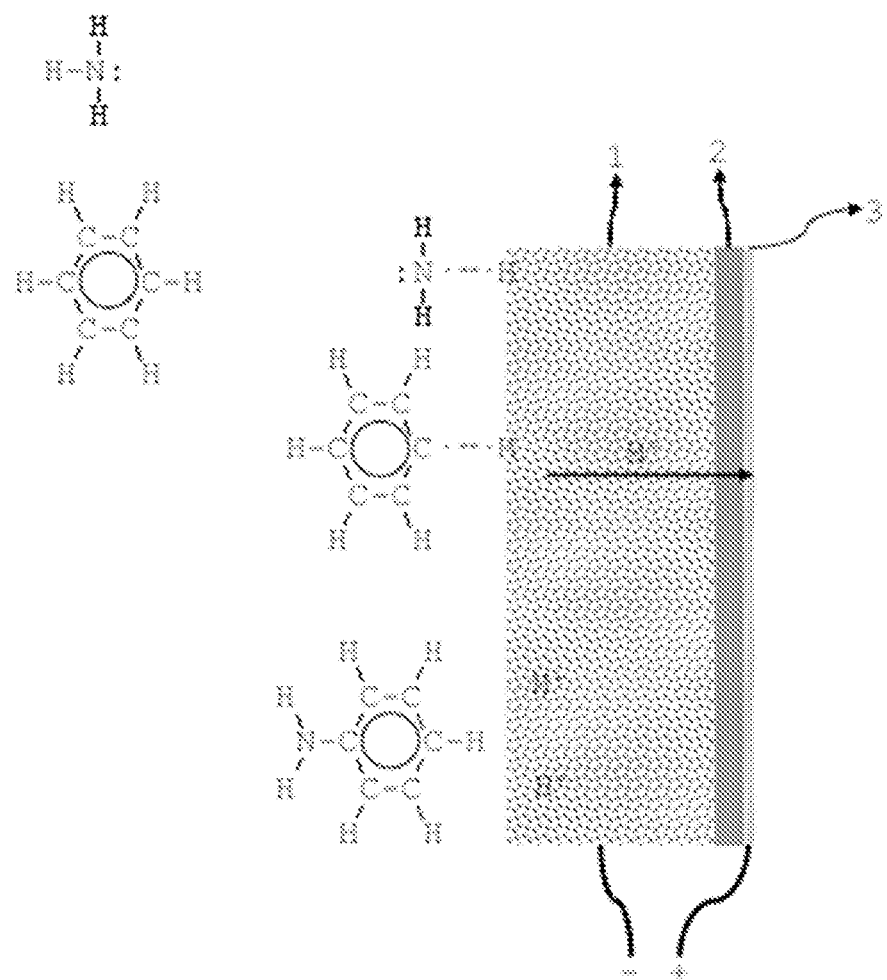
FIG. 2—Is a schematic representation of the cell or electrodes/electrolyte assembly and of the reaction scheme:
- (1)—Represents the electrode in contact with the reaction medium—anode;
- (2)—Represents the electrolyte;
- (3)—Represents the electrode—cathode.
Figure 3:
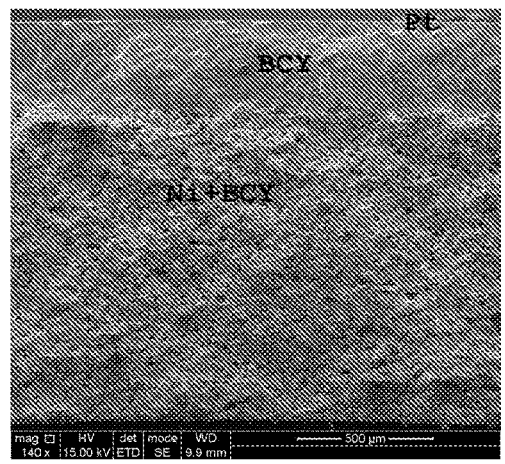
Figure 3:
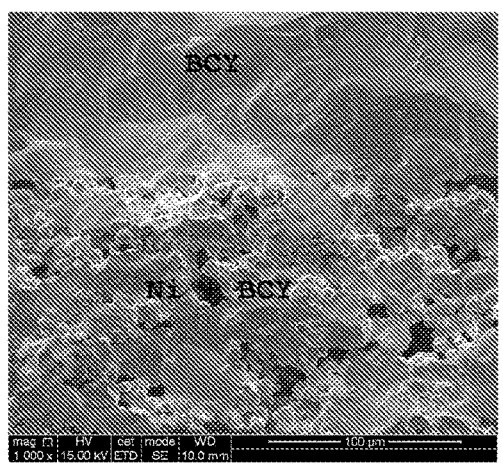
Figure 3:
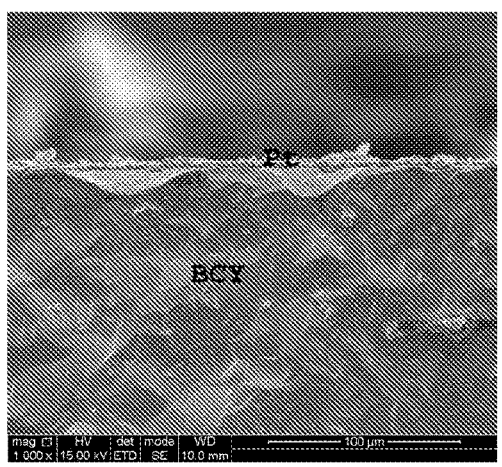

FIG. 3—Photographs of scanning electronic microscopy (SEM) of the electrodes/electrolyte assembly (MEA), where the electrolyte layer (BCY), the electro anode (Ni+BCY), and the electro cathode (Pt) are visible. a) overall image, b) detailed image of the interface electro anode/electrolyte, c) detailed image of the interface electro cathode/electrolyte.

DETAILED DESCRIPTION

The present invention describes a cell or electrodes/electrolyte assembly, and an electrochemical reactor, that comprises the electrodes/electrolyte assembly (MEA) for the direct amination of hydrocarbons, namely in the amination of benzene to aniline.

The electrodes/electrolyte assembly (MEA) is comprised by a ceramic electrolyte of solid oxide, and two porous layers positioned on each of its faces and constituting the anode and the cathode.

The anode (1) has the function of catalysing the chemical reaction of direct amination, catalysing the hydrogen oxidation reaction (both atomic or molecular), conducting the protons till the electrolyte and the electrons to the external electric circuit and promoting electrochemically a direct amination reaction.

For its part, the cathode (3) shall promote a reduction reaction of the permeate protons with the electrons from the external circuit, or a reaction of the protons with the oxygen fed to the cathode, and the electrons from the external circuit.

The electrolyte (2) has the function of permeating the protons and imposing a barrier to the permeation of reagents and reaction products and of the conduction of electrons.

This application describes the preparation of electrodes/electrolyte cells or assemblies (MEA) for use in electrochemical reactors, employed for direct amination of hydrocarbons, namely of benzene. The reaction of direct amination of benzene to aniline is described by the following equation:

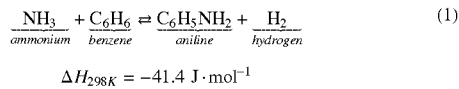

$$\underset{ammonium}{NH_3} + \underset{benzene}{C_6H_6} \rightleftharpoons \underset{aniline}{C_6H_5NH_2} + \underset{hydrogen}{H_2} \quad (1)$$

$$\Delta H_{298K} = -41.4 \; J \cdot mol^{-1}$$

This reaction is strongly limited by the thermodynamic equilibrium. The production of aniline via direct amination is only economically feasible if it is possible to significantly increase the conversion of the reaction (1). This conversion can be improved by the removal of formed hydrogen. The most efficient way to conduct this removal is using an electrochemical pumping reactor of hydrogen.

However, the efficient removal of hydrogen from the reaction medium is not sufficient by itself to obtain industrially attractive conversions, that is, conversions typically above 20%, and desirably above 50%.

Thus, the present invention discloses the preparation of MEAs that, insert into a membrane electrochemical reactor, allow not only the electrochemical pumping of atomic hydrogen resulting from de amination reaction, but also the electrochemical promotion of the amination reaction, by improving the conversion and the selectivity of the reaction to values above 60%.

The cell or electrodes/electrolyte assembly (Membrane Electrode Assembly—MEA) comprises the following elements:
  A ceramic electrolyte of solid oxides (2) (protons or ions conductive) located between two porous layers composing the anode and the cathode. The electrolyte (2) must be non-porous, i.e., impermeable to reagents and reaction products;
  The porous layer of the anode (1), preferably comprised of a metal oxide (e.g., nickel oxide—NiO), which after being reduced to the metallic form promotes the reaction of direct amination of benzene, the electrochemical promotion of the amination reaction and an electro oxidation of the produced atomic or molecular hydrogen. The metallic oxide is supported on a solid oxide—Ceramic—protons conductive (e.g., barium cerate doped with yttrium—BCY), that promotes a conduction of protons resulting from the reaction to the electrolyte, comprised by the protons conductor, preferably solely constituted by this one;
  Finally, the cathode (3) comprises a proton and electron thin conductive layer, and an electro catalyst which promotes the reduction of permeate protons. The protons reduction can be made by direct reaction with the electrons from the external circuit or with the oxygen, if available on the cathode side. Typically, the cathode is a thin layer of platinum nanoparticles applied directly to the electrolyte (2) and connected thereto after sintering. Another configuration uses a thin layer of a mixture of nanoparticulated platinum and BCY, applied on the electrolyte, and connected thereto after sintering.

A ceramic/metallic MEA shall be inserted in an electrochemical reactor, which shall comprise one or more electrochemical cells. Each electrochemical cell may comprise the above described electrodes/electrolyte assembly (MEA), which may be planar or tubular, an anode chamber, where the amination reaction takes place, and a cathode chamber, where the reduction of protons occurs. In an electrochemical cell, which has a very similar configuration to the solid oxide fuel cell—SOFC, the anode is electrically connected with the cathode through an external electric circuit. Once that it is pretended to promote the electrochemical pumping of hydrogen, atomic or molecular, and the electrochemical promotion of the amination reaction, it is necessary to feed electric power to the cell. The necessary difference of potential, that shall be supplied to the electrochemical cell, is limited above by the potential of electro oxidation of the benzene to products other than aniline and the lower level by the over voltages associated with the oxidation and reduction of hydrogen, electrochemical promotion of amination and ohmic resistance of the protons transport. On the other hand, the applied difference of potential must be selected depending on the temperature of the amination reaction and in a way to avoid deep dehydrogenation of benzene and subsequent formation of coke. The difference of potential to be applied may be higher than 0.2 V and lower than 1.5 V, preferably between 0.5 V and 1 V. So the cathode gives an output stream of molecular hydrogen.

In the case of being supplied to the cathode a gas stream containing oxygen, the protons, when reacting with oxygen and electrons from the external circuit, do origin a difference of potential that is enough for the electrochemical pumping of hydrogen and the promotion of electrochemical amination, being in this case unnecessary to feed electric power to the reactor. The product of this reaction is in this case water vapour. As mentioned before, this concrete embodiment is only possible if for the observed voltage a deep dehydrogenation of the reagents doesn't occur.

The reactor could operate at the maximum possible temperature, in the case of direct amination from benzene to aniline, lower than the temperature of decomposition of benzene and of aniline (about 400° C., in the case of use of a nickel containing catalyst). The protonic conductivity of the electrolyte increases with temperature as well as the kinetics of amination. Temperatures below 400° C. are also privileged, as there are low cost and high performance materials industrially available for the construction of electrochemical cells, particularly in what regards sealing. The operation temperature of the amination reactor may range between 250° C. and 450° C., preferably between 350° C. and 400° C.

Since the conversion of the reaction per unit volume of reactor increases with the pressure of the reaction medium (anode), the pressure of the anode could be the highest allowed for the materials of the electrochemical reactor and by its compression costs. This operating pressure shall range between atmospheric pressure and 300 bar, more preferably between 7 bar and 30 bar.

Electrolyte

The electrolyte layer (2) shall be non-porous, i.e., its porosity shall be such that does not allows the permeation of reagents and products between the anode and the cathode. The electrolyte (2) has, as its main function, the physical separation of the reagents fed to the anode side (1) and to the cathode side (3); to ensure electrical isolation between the two electrodes, forcing the electrons formed at the anode (1) to circulate through an external circuit to the cathode (3); allow the transport of protons formed during the electro oxidation of hydrogen (atomic or molecular) in the amination reaction, from the anode (1) to the cathode (3).

The ceramic oxides electrolyte (2) shall present high protons conduction, and this conductivity can be greater than 50 $\mu S \cdot cm^{-1}$ at operation temperatures; it shall present a high degree of densification, i.e, shall present a negligible porosity, such that it is impermeable to the reagents and products of the amination reaction; being impermeable, in the case of the direct amination of benzene to aniline: to benzene, ammonia, aniline, to the atomic or molecular hydrogen, to oxygen and to nitrogen; it shall further have high mechanical and thermal resistance and present a thermal expansion compatible with the electrodes; it shall have chemical compatibility with chemical reagents and reaction products and have electrochemical stability when subjected to the applied difference of potential.

The materials used in the preparation of the electrodes/electrolyte assembly have optimal protons conductivity inside the range of temperatures from 300° C. to 600° C. It was found that ceramic oxides of barium cerate doped yttrium (BCY) type have very high protons conductivity and are compatible with the direct amination reaction.

Anode

The electro anode or anode (1) contacts the reagents of the amination reaction (i.e., the reaction medium) and the electrolyte. The electro anode (1) is a composite layer located on one side of the electrolyte to promote the reaction of direct amination of benzene, oxidation of hydrogen (atomic or molecular), the conduction of protons to the electrolyte and of the electrons to the external electric circuit. The electro anode is porous, with metallic catalyst nanodispersed, in order to ensure a wide area where the amination reaction can occur, increasing synergistically the reaction yield at low temperatures.

The anode (1) shall thus be simultaneously electrons and protons conductive. In a preferential embodiment, the composite matrix that comprises the anode, is usually formed by a metallic oxide (e.g., nickel oxide—NiO), later reduced to its metallic form, and supported on a solid oxide proton conductor. This is the typical configuration of a cermet comprised of a metal and a ceramic protons conductor. The electrochemical reaction of oxidizing hydrogen (atomic or molecular) occurs inside the triple phase boundaries, preferably catalyzed by the nickel catalyst which is simultaneously catalyst of the chemical reaction of direct amination of benzene. Nickel is also a chemical and electrochemical catalyst that allows a promotion of direct amination reaction of benzene, the oxidation of hydrogen atoms as they are removed from de reagents, in order to originate the intermediate species which will react to produce the aniline, and its transportation to out of the reaction region under the action of the applied electric field. The removed hydrogen atoms, in form of protons, are conducted through the ceramic phase of the anode, to the electrolyte and from this to the cathode, where they are reduced to molecular hydrogen, or made to react with oxygen to form water. The directing force for an electrochemical reaction is the difference of potential imposed between the anode and the cathode, or the difference of potential generated by the electrochemical reaction of protons permeated with the oxygen available in the cathode and the electrons from the external electric circuit.

The electrons conductivity of the anode (1) is related with the percolation through the nanoparticles of the metallic catalyst, preferably Ni, and therefore dependent on the concentration of the metal and on the protons conductor. For example, below the percolation threshold of Ni (about 30% (v/v) to 40%(v/v)), the cermet has essentially protons conductivity. On the other hand, above the threshold of percolation, the conductivity of the cermet is mostly for electrons, promoting the conduction of the electrons formed to the external circuit.

The porosity of the anode layer (1) measures the fraction of volume occupied by pores (which diffuse reagents and reaction products) in relation to the total volume of the anode (1).

The determination of the porosity can be experimentally effected by methods usually accepted as, for example, by the mercury porosimetry method [3]. Usually porosimetry is attained by reducing metal oxide to metallic form. However, the simple reduction of metallic oxide can be insufficient to originate an increased porosity for the diffusion of the reagents, preferably ranging from 10% to 40% inclusively. The additional porosity can be obtained through the addition of eliminated substances during a calcination of the MEA. These substances are additives that have the double function of facilitate the mixing of the proton and electronic conductive phases and the catalyst and formation of the electrode, function of binder/dispersant, and that of imparting porosity. In general these additives are starches various cereal or synthetic polymers, i.e. organic additives, preferably polymers which evaporate without leaving a trace at temperatures up to 900° C., such as PVA (polyvinyl alcohol). Corn starch is generally preferred as pore forming compound in that it presents a geometric shape similar to that of the anode and electrolyte precursor powders, is easily removed at temperatures well below the sintering temperatures and simultaneously functions as binder for the ceramic powders. Furthermore, it's an abundant and low cost raw material.

Cathode

The cathode or electro-cathode (3) shall promote a conduction of electrons from external circuit to the interface, where a reduction reaction of protons or their reaction with oxygen for the production of water vapour, occurs. As the electro-anode (1), the electro-cathode (2) shall present a porous structure and have mixed conductivity (ionic and electronic). In a preferred embodiment, the cathode (3) comprises a metal catalyst that promotes the reduction of protons to molecular hydrogen or the recombination of these protons with oxygen and electrons to form water vapour (e.g., platinum) supported on a proton conductor (e.g., BCY).

Fabrication of MEA

In a preferred embodiment, the anode (1) shall have a thickness above that of the electrolyte (2), and of the cathode (3), in order to provide a high catalytic area; on the other hand, the anode porosity allows for an efficient mass transfer to the reagents and amination reaction products. In a preferred embodiment, the electrodes/electrolyte assembly shall be as thin as possible in order to have high proton conductivity and thus allow installing electrochemical cells with high efficiency and lower ohmic losses in the direct amination of hydrocarbons, preferably in the production of aniline.

The thickness of the electrodes/electrolyte assembly shall be, in a preferred embodiment, limited only by its mechanical strength and by its barrier effect against the reagents and reaction products, preferably with thicknesses between 100 µm and 2000 µm, more preferably between 300 µm and 400 µm inclusively. The planar configuration of a MEA is usually preferred, allowing the use of cheaper manufacturing methods. From the more used methods stands out the method of uniaxial pressing powders of metal oxides or ceramic oxides and the method of wet powder spraying, due to their practical and economic viability.

In a preferred embodiment, the method to obtain the above described electrodes/electrolyte assembly comprises the following steps:

mixing of the anode precursor powders: metallic oxide (e.g., NiO, with a medium diameter of 50 nm) and protons conductor (e.g., BCY, with a medium diameter of 400 nm), and an organic additive (e.g. corn starch). The proportion of metal oxide on the ions conductor varies from about 30% (w/w) to 70% (w/w) and the concentration of corn starch powder in the mixture varies between 5% (w/w) and 30% (w/w). The powders can be mechanically mixed in a ball mill or manually in a mortar. Grinding can be conducted in the presence of a solvent (e.g., isopropanol).

The resulting mixture is then formed in a mould and pressed on a uniaxial press, cold or with heated plates, at a temperature between about 85° C. and 150° C., preferably about 90° C., so as to evaporate the solvent. The pressure applied on the disk varies between 550 bar and 1100 bar for 5 min to 15 min.

The deposition of dry powder protonic conductor is then carried out (e.g., BCY, with a medium diameter of 400 nm) on the layer of the anode and pressing of the disc on the double-layer. The pressure applied to the double-layer varies between 1100 bar and 1500 bar.

The double layer is finally co-sintered at a temperature ranging from 1300° C. to 1600° C., during 5 h to 24 h, with a heating rate varying from 1° C.·min$^{-1}$ to 5° C.·min$^{-1}$, in an oxidising atmosphere.

The deposition of the electro-cathode (3), preferably platinum, on the double-layer of anode/electrolyte can also be effected by the method of co-pressing and co-sintering. However, in configurations of the electrolyte type (2) supported on the anode, the deposition of the porous cathode can be achieved by the method of wet powder spraying. The method consists in the preparation of a Pt/BCY suspension in an alcoholic solution of PVB (polyvinyl butyral) and its deposition on the electrolyte, using a manual aerograph, followed by a drying step. For the same configuration, the cathode layer can be obtained by manual application of a commercial platinum paste (nanodispersed platinum in a solvent and binders, for example Heraeus CL11-5349). For both deposition alternatives of the cathode, the electrodes/electrolyte assembly is finally sintered at a temperature that varies between 900° C. and 1100° C., preferably for 2 h and at a heating rate of between 1° C. min$^{-1}$, and 5° C. min$^{-1}$ in the presence of oxygen. The number of layers applied to the cathode (3), preferably platinum, is made in accordance with the desired thickness and conductivity. The application of each layer is followed by a sintering step.

After the sintering step, the electrodes/electrolyte assembly can be placed directly in the electrochemical reactor, feeding $H_2$ at a temperature that varies from 400° C. to 1000° C.

Reaction of Direct Amination of Benzene

In other embodiments, the global reaction for production of aniline by direct amination of benzene with ammonia is represented by the equation (1). However, the reactional scheme involves several steps that consist in the activation (breakage) of the simultaneous bonds C—H and N—H, respectively from benzene and from ammonia. The activation of those bonds is allowed by the use of transition metal catalysts (e.g., Ni, Pd and Pt). The C—H bond activation occurs when the benzene undergoes a process of physical adsorption at the surface of the metal catalyst, followed by chemical adsorption on the same catalyst, yielding a highly reactive compound, the phenyl radical (.$C_6H_5$). Activation of the ammonia N—H bond is harder than the former, once that it is a stronger bond (107 kcal·mol$^{-1}$). In a first stage the $NH_3$ suffers also an adsorption on the catalyst surface, leading to breakage of one bond N—H. The electrophilic attack is performed by the ammonia adsorbed on metallic catalyst, which loses its nucleophilic character (due to the unpaired pair of electrons of the nitrogen atom); .$NH_2$ radical reacts with the phenyl radical to give a molecule of aniline. The formed aniline is then removed from the reaction medium through the porosity of the electro anode. Other reaction schemes are possible although having in common the formation of intermediate reaction species after losing the atomic hydrogen in form of radicals. The hydrogen radicals are formed in the adsorbed phase on the surface of the metallic catalyst.

The formed pair of hydrogen radicals (.H) is electro oxidised and the resulting protons are transported through the ceramic phase of the electro anode to the electrolyte, and the electrons are transported through the metallic phase of the electro anode to the external circuit. In case that the radical pair ● H forms molecular hydrogen, this one is adsorbed on the metal phase of the electro anode, oxidizing to protons that are conducted through the ceramic phase to the electrolyte. The directing force of the electrochemical reaction is the difference of electric potential imposed to the electrodes or resulting from the reaction of the permeated protons current with the oxygen in the electro cathode.

The formation of radicals is electrochemically promoted by the electric field established between the anode and the cathode, which results in the modification of the surface of the catalyst [4]. The process herein disclosed for direct amination only exceptionally will allow the formation of molecular hydrogen. In other former preferred embodiments, and taking advantage in that the chemical catalyst for the amination reaction is the same as the electrocatalyst for the oxidation of hydrogen, preferably nickel, adsorbed hydrogen radicals, when being formed, are immediately oxidized to protons and transported through the electro anode to the electrolyte and from this to the electro cathode, where they undergo reduction or react with oxygen, as described before. Finally, if there is formation of molecular hydrogen, it is easily oxidized to protons and thus removed from the reaction medium. As mentioned above, with the present invention an increase of conversion of the direct amination reaction of benzene is verified, based on the uptake of hydrogen radicals formed during the reaction of benzene with ammonia and protons and its electro oxidation to protons and consequent prompt removal from the reaction medium. In a preferred embodiment, the reaction temperature of the amination of benzene on nickel shall be as high as possible, to allow fast reaction kinetics and also high protons conductivity. However, in a preferred embodiment, this temperature should not exceed 400° C., since at this temperature the occurrence of CHx- fragments begins and afterwards the formation of coke, resulting from the decomposition of benzene. Above 350° C. it begins to be observed the appearance of benzonitrile and compounds resulting from complete decomposition of the $NH_3$. Thus, the preferred reaction temperature is between 200° C. and 450° C., more preferably between 300° C. and 400° C.

On the other hand, in a preferred embodiment the difference of potential imposed shall be the highest possible, in order to be obtained a high protons transportation. This difference of potential shall be limited by the costs of energy and by the electrochemical dehydrogenation of benzene. The preferred difference of potential is thus between 0.2 V and 1.5 V.

In a preferred embodiment, the electrodes/electrolyte assembly (MEA) is prepared by the co-pressing and co-sintering method. The anode layer is prepared with a mixture of NiO (Alfa Aesar, Ref. 45094, green, Ni 78.5%) and BCY (TYK Co.) for a final composition of 40% (w/w) of Ni. 10% (w/w) of corn starch are further added to the dry powder mixture. This mixture is grinded in an agate mortar, and finally cold formed in a metal mould with the aid of an uniaxial press at 1100 bar. The electrolyte layer is obtained by means of the deposition of dry powder of BCY (TYK Co.) on a layer, which constitutes the anode. The double layer is compressed at 1500 bar and sintered at 1400° C. for 5 h. Finally the cathode is deposited on the other face of the electrolyte through the application of a commercial platinum paste—Pt (Heraeus CL11-5349), and sintered at 900° C. for 2 h. The MEA is then introduced into the electrochemical reactor, where NiO undergoes reduction to Ni in presence of $H_2$ at 400° C. The protons conductivity of BCY, obtained at 400° C., is 4.60 $mS \cdot cm^{-1}$. To the cathode side a nitrogen current is fed and a difference of potential of 1.2 V is imposed to the cell, corresponding to a $H_2$ permeate flow rate of 2.25 $\mu mol \cdot s^{-1}$.

In a preferred embodiment, the electrodes/electrolyte assembly (MEA) is prepared by the above described co-pressing and co-sintering method, and set into the electrochemical reactor. The temperature of the reactor is set to 400° C. After reduction of NiO to Ni in presence of $H_2$, an equimolar current of $C_6H_6$ and $NH_3$ is fed to the anode side. The reaction temperature is 400° C., and the products are condensed at the exit of the anode chamber. To the cathode side a current of nitrogen is fed in order to maintain the pressure of both chambers substantially equivalent. The observed conversion of benzene to aniline is 0.5%. After imposition of a difference of potential of 1.2 V to the electrochemical cell, a rate of conversion of 60% is obtained from the reaction of benzene to aniline.

REFERENCES

[1]—D. Z. de Florio, F. C. Fonseca, E. N. S. Muccillo, R. Muccillo, "Materiais cerâmicos para células a combustível" ["Ceramic materials for fuel cells"], Cerâmica, 50, 275-290, 2004.

[2]—R. S. Amado, L. F. B. Malta, F. M. S. Garrido, M. E. Medeiros, "Pilhas a combustível de óxido sólido: materiais, componentes e configurações" ["Fuel piles of solid oxide: materials, components and settings"], Química Nova, 30, 189-197, 2007.

[3]—S. Gregg, K. S. W. Sing, "Adsorption, Surface Area and Porosity", 2nd ed., Academic Press, London, 1982.

[4]—C. G. Vayenas, S. Brosda, C. Pliangos, "Rules and Mathematical Modelling of Electrochemical and Chemical Promotion: 1. Reaction Classification and Promotional Rules", Journal of Catalysis, 203, 329-350, 2001.

The present invention is not, of course, restricted in any way to the embodiments described herein and a person with ordinary skill in the area can provide plenty of changes without departing from the general idea of the invention, as defined by the claims.

The above described preferred embodiments are obviously combinable with each other. Additionally, the following claims define preferred embodiments of present invention.

The invention claimed is:

1. Electrodes/electrolyte assembly for direct amination of aromatic hydrocarbons that comprises:
   a simultaneously electron and proton conductive anode comprising
      a composite porous matrix, the composite porous matrix comprising a proton conductive ceramic fraction, wherein the ceramic fraction is barium cerate doped with nanoparticulated yttrium, and
      a metal catalyst for said direct amination of aromatic hydrocarbons at temperatures lower than 450° C., wherein the metal catalyst comprises nickel, nickel oxide or mixtures thereof, and wherein the porosity of the anode ranges between 10-40%;
   an electrocatalyst porous cathode having protonic and electronic conductivity comprising an electrocatalyst;
   a proton or ion conductive and electrically insulated electrolyte located between the anode and the cathode, made of a composite ceramic impermeable to reagents and to the products of said direct amination of aromatic hydrocarbon,
   wherein the anode and the cathode are electrically connected, and
   wherein the anode comprises a higher catalytic area than a catalytic area of the electrolyte and the cathode combined.

2. The electrodes/electrolyte assembly according to claim 1, wherein the metal catalyst is nickel, the cathode is platinum and the electrolyte is barium cerate doped with yttrium.

3. The electrodes/electrolyte assembly according to claim 1, wherein the metal catalyst is nickel and the ceramic fraction is further doped with zirconium, the cathode is platinum and the electrolyte is barium cerate doped with yttrium and zirconium.

4. An electrochemical reactor with electrochemical pumping of hydrogen for the direct amination of aromatic hydrocarbons, which has at least one electrochemical cell, the at least one electrochemical cell comprising at least one electrodes/electrolyte assembly comprising:
   a simultaneously electron and proton conductive anode in an anode chamber, the anode comprising
      a composite porous matrix, the composite porous matrix comprising a proton conductive ceramic fraction, wherein the ceramic fraction is barium cerate doped with nanoparticulated yttrium and
      a metal catalyst for said direct amination of aromatic hydrocarbons at temperatures lower than 450° C., wherein the metal catalyst comprises nickel, nickel oxide or mixtures thereof, and wherein the porosity of the anode ranges between 10-40%;
   an electrocatalyst porous cathode in a cathode chamber having protonic and electronic conductivity comprising an electrocatalyst;
   a proton or ion conductive and electrically insulated electrolyte located between the anode and the cathode, made of a composite ceramic impermeable to reagents and to the products of said direct amination of aromatic hydrocarbon, wherein, direct amination of the aromatic hydrocarbon occurs in said anode chamber, and reduction of protons occurs in said cathode chamber, wherein the anode and the cathode of said electrodes/electrolyte assembly are electrically connected, and wherein the anode comprises a higher catalytic area than a catalytic area of the electrolyte and the cathode combined.

5. The electrochemical reactor according to claim 4, wherein the porosity of the anode ranges between 20-30%.

6. The electrochemical reactor according to claim 4, wherein the electrodes/electrolyte assembly comprises a planar or tubular configuration.

7. The electrochemical reactor according to claim 4, wherein the metal catalyst of the anode further comprises at least one doping element selected from the group consisting of aluminium, cobalt, copper, chromium, tin, strontium, iron, gadolinium, indium, iridium, yttrium, lanthanum, lithium, manganese, molybdenum, niobium, gold, palladium, platinum, silver, praseodymium, ruthenium, titanium, zinc, and mixtures thereof.

8. The electrochemical reactor according to claim 4, wherein the barium cerate doped with yttrium is further doped with zirconium.

9. The electrochemical reactor according to claim 4, wherein the anode further comprises nickel nanoparticles.

10. The electrochemical reactor according to claim 4, wherein the anode comprises an homogeneous mixture of:
30% (w/w) to 70% (w/w) of nickel oxide; and
70% (w/w) to 30% (w/w) of the barium cerate doped with nanoparticulated yttrium.

11. The electrochemical reactor according to claim 4, wherein the electrolyte comprises at least one element selected from the group consisting of aluminium, barium, calcium, cerium, copper, strontium, gadolinium, yttrium, indium, lanthanum, niobium, neodymium, praseodymium, samarium, titanium, zirconium, and mixtures thereof.

12. The electrochemical reactor according to claim 4, wherein the cathode comprises at least one metal selected from the group consisting of aluminium, cobalt, copper, chromium, tin, strontium, iron, indium, iridium, yttrium, lithium, manganese, molybdenum, niobium, gold, palladium, platinum, silver, ruthenium, titanium and zinc.

13. The electrochemical reactor according to claim 4, wherein the electrocatalyst of the cathode comprises nanoparticulate platinum or nanoparticulate platinum and barium cerate doped with yttrium.

14. The electrochemical reactor according to claim 4, wherein the cathode further comprises at least one oxide selected from the group consisting of aluminium, barium, calcium, cerium, copper, strontium, gadolinium, yttrium, lanthanum, niobium, neodymium, praseodymium, samarium, titanium and zirconium oxides.

15. The electrochemical reactor according to claim 4, wherein the thickness of the electrolyte ranges between 10 µm and 400 µm.

16. The electrochemical reactor according to claim 4, wherein a difference of potential between the anode and the cathode is lower than 1.5 V.

17. The electrochemical reactor to claim 4, wherein the metal catalyst is nickel, the cathode is platinum and the electrolyte is barium cerate doped with yttrium.

18. The electrochemical reactor according to claim 4, wherein the metal catalyst is nickel and the ceramic fraction is further doped with zirconium, the cathode is platinum and the electrolyte is barium cerate doped with yttrium and zirconium.

\* \* \* \* \*